(12) United States Patent
Weadock et al.

(10) Patent No.: US 9,855,164 B2
(45) Date of Patent: Jan. 2, 2018

(54) METHOD AND DEVICE FOR TREATING OBSTRUCTIVE SLEEP APNEA

(71) Applicant: Ethicon, Inc., Somerville, NJ (US)

(72) Inventors: Kevin Weadock, Hillsborough, NJ (US); Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 262 days.

(21) Appl. No.: 13/786,763

(22) Filed: Mar. 6, 2013

(65) Prior Publication Data
US 2014/0251343 A1 Sep. 11, 2014

(51) Int. Cl.
A61F 5/56 (2006.01)

(52) U.S. Cl.
CPC .................................. A61F 5/566 (2013.01)

(58) Field of Classification Search
CPC combination set(s) only.
See application file for complete search history.

(56) References Cited

U.S. PATENT DOCUMENTS

| | | | |
|---|---|---|---|
| 4,557,264 A | 12/1985 | Hinsch | |
| 5,176,618 A * | 1/1993 | Freedman | ........................ 600/12 |
| 5,284,161 A | 2/1994 | Karell | |
| 5,792,067 A | 8/1998 | Karell | |
| 6,183,493 B1 * | 2/2001 | Zammit | ........................ 606/196 |
| 6,328,753 B1 | 12/2001 | Zammit | |
| 6,589,225 B2 | 7/2003 | Orth | |
| 7,063,089 B2 | 6/2006 | Knudson | |
| 7,363,926 B2 * | 4/2008 | Pflueger | ................... A61F 2/203 |
| | | | 128/200.24 |
| 8,037,885 B2 * | 10/2011 | Metzger | .................... A61F 2/00 |
| | | | 128/848 |
| 8,074,655 B2 | 12/2011 | Sanders | |
| 2001/0050084 A1 | 12/2001 | Knudon et al. | |
| 2002/0002360 A1 | 1/2002 | Orth | |
| 2003/0199809 A1 | 10/2003 | Orth | |
| 2007/0144534 A1 | 6/2007 | Mery | |
| 2007/0144539 A1 | 6/2007 | van der Burg | |
| 2007/0261701 A1 | 11/2007 | Sanders | |
| 2008/0066766 A1 * | 3/2008 | Paraschac | ............... A61F 5/566 |
| | | | 128/848 |
| 2008/0188947 A1 | 8/2008 | Sanders | |

(Continued)

FOREIGN PATENT DOCUMENTS

EP 1981431 A2 10/2008
EP 1981431 A4 1/2012

(Continued)

Primary Examiner — Ophelia A Hawthorne

(57) ABSTRACT

Methods and devices comprised of a collapsible insert member and shaping member for treating obstructive sleep apnea are described. The insert member is placed in the tongue or other tissue forming the airway of the patient and has a lumen to accommodate the shaping member. The shaping member is inserted into the insert member by the patient just prior to sleep and removed upon waking. A variety of shaping members are available to treat patients on an individual basis, i.e., to match their particular anatomic condition that is causing their apnea or snoring. The shaping member can be made from nitinol, stainless steel, or any other known biocompatible implant material capable of providing a change in the tissue response to stress.

2 Claims, 19 Drawing Sheets

(56) References Cited

U.S. PATENT DOCUMENTS

| | | |
|---|---|---|
| 2009/0014012 A1 | 1/2009 | Sanders |
| 2010/0004659 A1 | 1/2010 | Hegde |
| 2010/0242967 A1 | 9/2010 | Burbank |
| 2011/0226264 A1* | 9/2011 | Friedman ................ A61F 5/566 128/848 |
| 2012/0138069 A1* | 6/2012 | Gillis ...................... A61F 5/566 128/848 |
| 2012/0234332 A1* | 9/2012 | Shantha ................. A61F 5/566 128/848 |
| 2013/0046329 A1 | 2/2013 | Burbank et al. |
| 2013/0074849 A1* | 3/2013 | Rousseau ............... A61B 17/06 128/848 |

FOREIGN PATENT DOCUMENTS

| | | |
|---|---|---|
| WO | WO2005082452 A1 | 9/2005 |
| WO | WO2007064908 A2 | 6/2007 |
| WO | WO2007092865 A2 | 8/2007 |
| WO | WO2007064908 A3 | 12/2007 |
| WO | WO2007092865 A3 | 12/2007 |
| WO | WO2008042058 A1 | 4/2008 |
| WO | WO2010005900 A1 | 1/2010 |
| WO | WO2010005900 A8 | 8/2010 |
| WO | WO2012082791 A2 | 6/2012 |
| WO | WO2012082791 A3 | 9/2012 |
| WO | WO 2013/011478 A1 | 1/2013 |

* cited by examiner

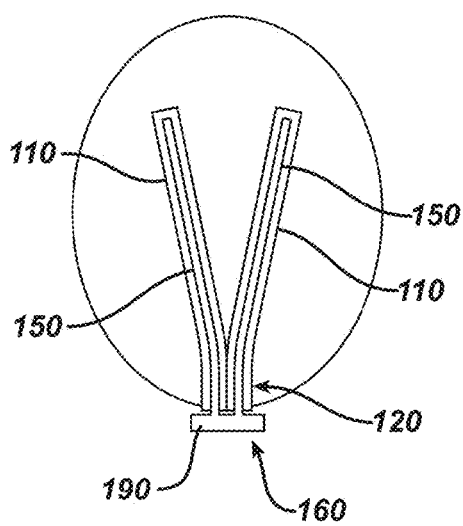 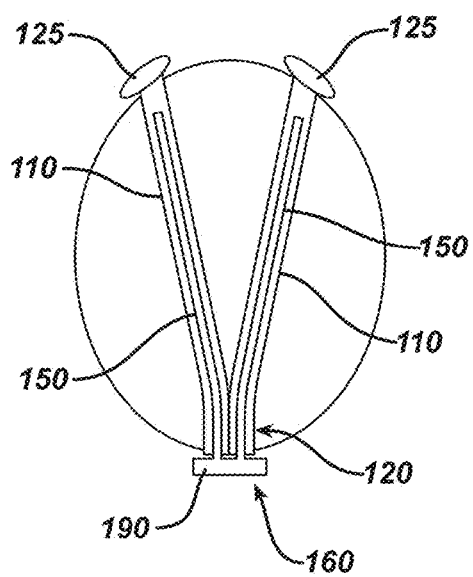

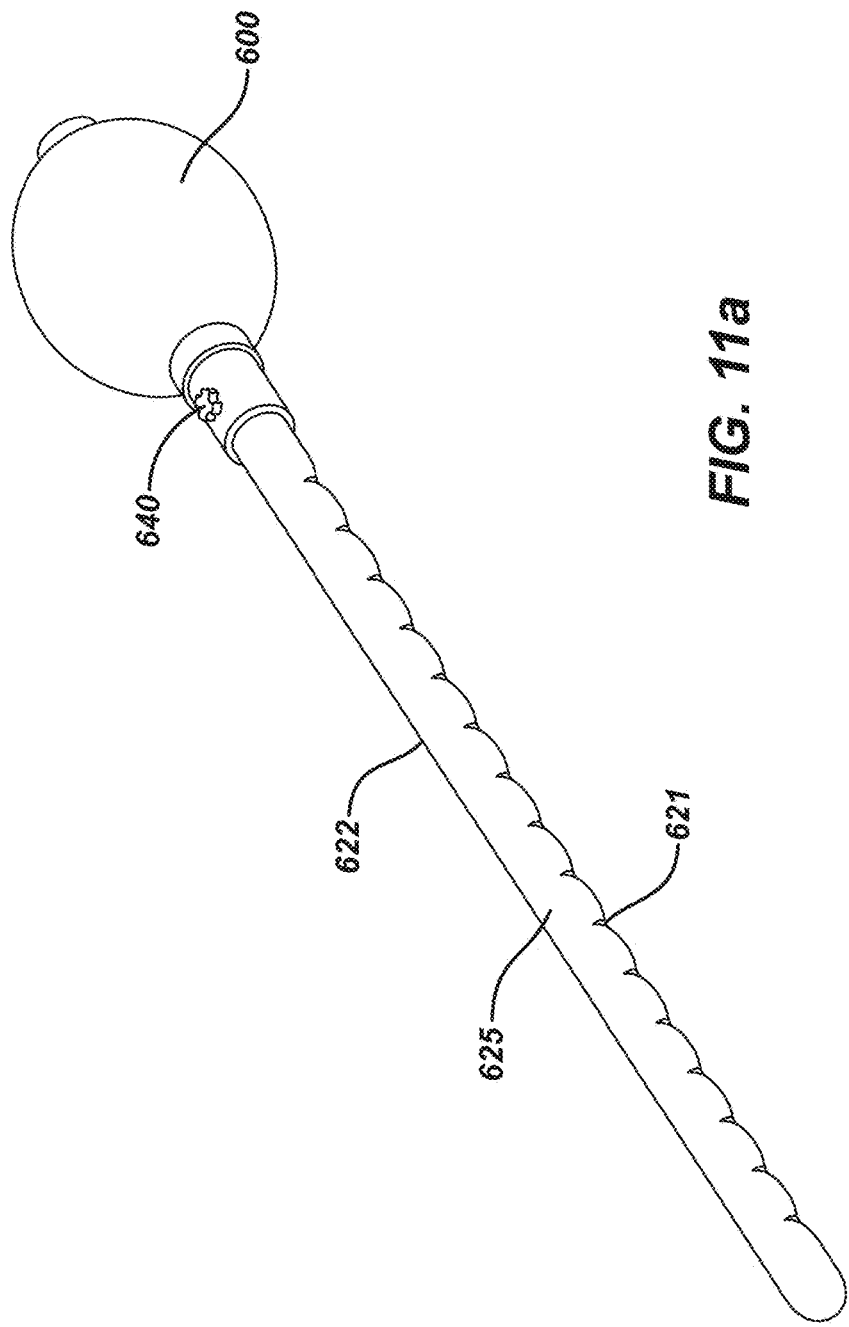

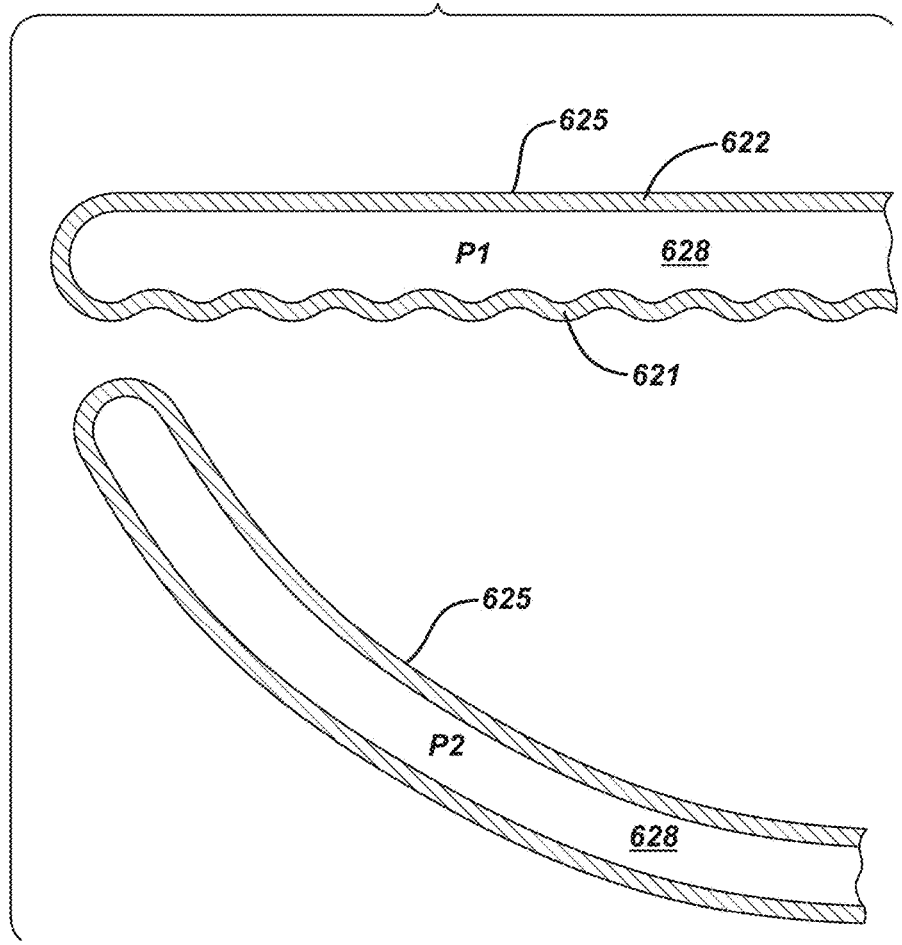

METHOD AND DEVICE FOR TREATING OBSTRUCTIVE SLEEP APNEA

FIELD OF THE INVENTION

The present invention generally relates to treating sleep disorders, and more specifically, relates to methods and devices for treating patients suffering from obstructive sleep apnea.

BACKGROUND OF THE INVENTION

Sleep disordered breathing describes a group of disorders such as snoring and obstructive sleep apnea and is characterized by abnormalities of respiratory pattern or the quantity of ventilation during sleep. Obstructive sleep apnea (OSA), the most common such disorder, is characterized by the repetitive collapse or partial collapse of the pharyngeal airway during sleep and the need to arouse to resume ventilation. Sleep is thus disrupted, yielding waking somnolence and diminished neurocognitive performance. The recurrent sleep arousal in association with intermittent hypoxia and hypercapnia has been implicated in the occurrence of adverse cardiovascular outcomes. In addition, there is evolving evidence that obstructive sleep apnea may contribute to insulin resistance and other components of the metabolic syndrome. Despite considerable progress, most patients remain undiagnosed and the principal therapeutic approach, continuous positive airway pressure (CPAP), remains somewhat cumbersome and hence not associated with optimal compliance rates.

Obstructive sleep apnea is caused by a blockage of the airway, which usually occurs when the soft tissue in the throat collapses and closes during sleep. FIG. 1 shows a cross-section of the naso-pharyngeal N area of a human. The mouth M and tongue T are shown along with a hard palate HP that separates the oral cavity from the nasal cavity. The soft palate SP extends from the hard palate HP and terminates by forming a uvula UV. Below the soft palate SP, the pharyngeal wall PW defines the throat passage TP. Below the epiglottis EP, the throat passage TP divides into a trachea TR for passing air to the lungs and an esophagus ES for passing food and drink to the stomach. The epiglottis EP closes the trachea TR during swallowing and drinking and opens for breathing.

During each apnea event, the brain briefly arouses the sufferer in order to initiate the resumption of breathing, however, this type of sleep is extremely fragmented and of poor quality. When left untreated, sleep apnea may result in high blood pressure, cardiovascular disease, weight gain, impotency, headaches, memory problems, job impairment, and motor vehicle crashes.

According to the National Institutes of Health, OSA is rather common and affects more than twelve million Americans. OSA affects males more than females. Other risk factors include being overweight and over the age of forty. Sleep apnea, however, can strike anyone at any age, even children. Despite the seriousness of OSA, a lack of awareness by the public and healthcare professionals results in the vast majority of patients remaining undiagnosed and untreated.

Continuous positive airway pressure (CPAP), which delivers air into the airway through a specially designed nasal mask or pillow, has been adopted as a treatment for obstructive sleep apnea. The flow of air creates positive pressure when the patient inhales to keep the airway open. CPAP is considered by many to be the most effective non-surgical treatment for the alleviation of snoring and obstructive sleep apnea, however, patients complain about discomfort from the mask and hoses, including bloating, nasal drying, and dry eyes. As a result, patient compliance is only about 40 percent.

Surgical treatments have also been employed. One such treatment is referred to as uvulopalatopharyngoplasty (UPPP), which involves removing about 2 cm of the trailing edge of the soft palate to reduce the soft palate's ability to flutter between the tongue and the pharyngeal wall of the throat. The procedure has been effective in alleviating snoring, but is painful and frequently results in undesirable side effects. In particular, removal of the trailing edge of the soft palate compromises the soft palate's ability to seal off nasal passages during swallowing and speech. As a result, in 25 percent of patients receiving UPPP, fluid escapes from the mouth and flows into the nose while drinking.

Another surgical procedure uses a laser to create scar tissue on the surface of the soft palate. The scar tissue reduces the flexibility of the soft palate, which, in turn, reduces snoring and/or closing of the air passage. Cautery-assisted palatal shaping operation (CAPSO) is a recently developed office-based procedure performed with local anesthesia. A midline strip of soft palate mucosa is removed, and the wound is allowed to heal. The flaccid palate is stiffened, and palatal snoring ceases.

Other surgical approaches have been tried that employ the use of RF or microwave energy (Somnoplasty) to shrink tissue in the tongue or soft palate. Radiofrequency ablation of the soft palate is used to produce thermal lesions within the tissues. Somnoplasty devices have been approved by the U.S. Food and Drug Administration (FDA) for radiofrequency ablation of palatal tissues for simple snoring and for the base of the tongue for OSA. In some situations, radiofrequency of the soft palate and base of tongue are performed together as a multilevel procedure. To date, the treatments alone or in combination have failed to provide relief to more than 50 percent of patients suffering from obstructive sleep apnea.

Another device intended to treat snoring or obstructive sleep apnea uses several braided PET cylinders that are implanted to make the tissues of the tongue or uvula more rigid and less prone to deflection against the pharyngeal wall. The Pillar™ Palatal Implant System sold by Restore Medical of St. Paul, Minn., is an implantable device that has been cleared by the FDA. The device is a cylindrical-shaped segment of braided polyester filaments that is permanently implanted submucosally in the soft palate, for reducing the incidence of airway obstructions in patients suffering from mild to moderate obstructive sleep apnea. The Pillar device has been associated with a number of adverse side effects, including extrusion, infection, and patient discomfort.

Another implant system sold under the trademark AIRvance™ tongue suspension system by Medtronic ENT, Jacksonville, Fla. employs a titanium screw that is inserted into the posterior aspect of the mandible at the floor of the mouth. A loop of suture is passed through the tongue base and attached to the mandibular bone screw. The AIRvance™ procedure achieves a suspension or hammock of the tongue base making it less likely for the base of the tongue to prolapse during sleep. Due to the high activity of the tongue during wakefulness, the suture component of this device has been shown to act as a "cheese cutter" to the tongue, causing device failure and requiring subsequent removal. Thus, the duration of beneficial effects afforded by the implant is short lived.

Surgical procedures such as UPPP and those mentioned above are painful with extended and uncomfortable healing periods. For example, scar tissue on the soft palate may present a continuing irritant to the patient. Moreover, the procedures are not reversible in the event they happen to induce adverse side effects. As a result, there have been a number of other approaches to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and may result in the repeated arousal of the patient. Magnets implanted at various sites in the airway in an attempt to provide forces for manipulating tissue have also been considered for treating sleep apnea. These devices have shown limited success due to implant migration, inability to control the degree of tissue manipulation or treatment, and that the devices only provide temporary results.

In spite of the above efforts, no one device has been used to effectively treat obstructive sleep apnea. Thus, there remains a need for methods and devices that reduce the burden of managing obstructive sleep apnea through minimally invasive approaches that provide long term results, encourage patient compliance, and minimize patient discomfort.

SUMMARY OF THE INVENTION

A device for treating obstructive sleep apnea having a collapsible insert member and a shaping member is disclosed. The insert member has a proximal end and a distal end and a lumen there between. The shaping member has a proximal end and a distal end, wherein the lumen of the insert member is adapted to receive at least a portion of the shaping member so as to provide a predetermined shape to the tongue that will resist movement that may cause an apneic event.

A method for treating obstructive sleep apnea involves providing a collapsible insert member having a proximal end and a distal end, and a lumen there between so that a shaping member having a proximal end and a distal end can be inserted into it. The method also includes using a needle having a lumen and a guidewire sized to pass through the lumen of the needle so as to create a channel for the insert member. The method further involves the steps of inserting at least a portion of the needle into a patient's tongue, inserting at least a portion of the wire into the lumen of the needle, removing the needle from the patient's tongue, positioning the lumen of the insert member over the wire, advancing at least a portion of the insert member into the patient's tongue, removing the wire from the patients tongue, and inserting at least a portion of a shaping member into the lumen of the insert member so that the insert member and shaping member interact to distribute a force on at least a portion of the patient's tongue.

BRIEF DESCRIPTION OF THE FIGURES

FIG. 9a illustrates an embodiment of the invention wherein two insert members are installed intra-tongue, or do not pass completely through the tongue.

FIG. 9b illustrates an embodiment of the invention wherein two insert members are installed completely through the tongue.

FIG. 11a illustrates an embodiment of the invention wherein the shaping member comprises a bulb assembly and a pressure receiver chamber.

FIG. 11c illustrates pressurization of the non pressure receiver chamber shown in FIGS. 11a and 11b, wherein P1 represents the initial fluid pressure within the lumen of the pressure receiver chamber, and P2 represents the pressure of the fluid within the lumen of the pressure receiver chamber after pressurization and is greater than P1.

DETAILED DESCRIPTION OF THE INVENTION

Figure 1:
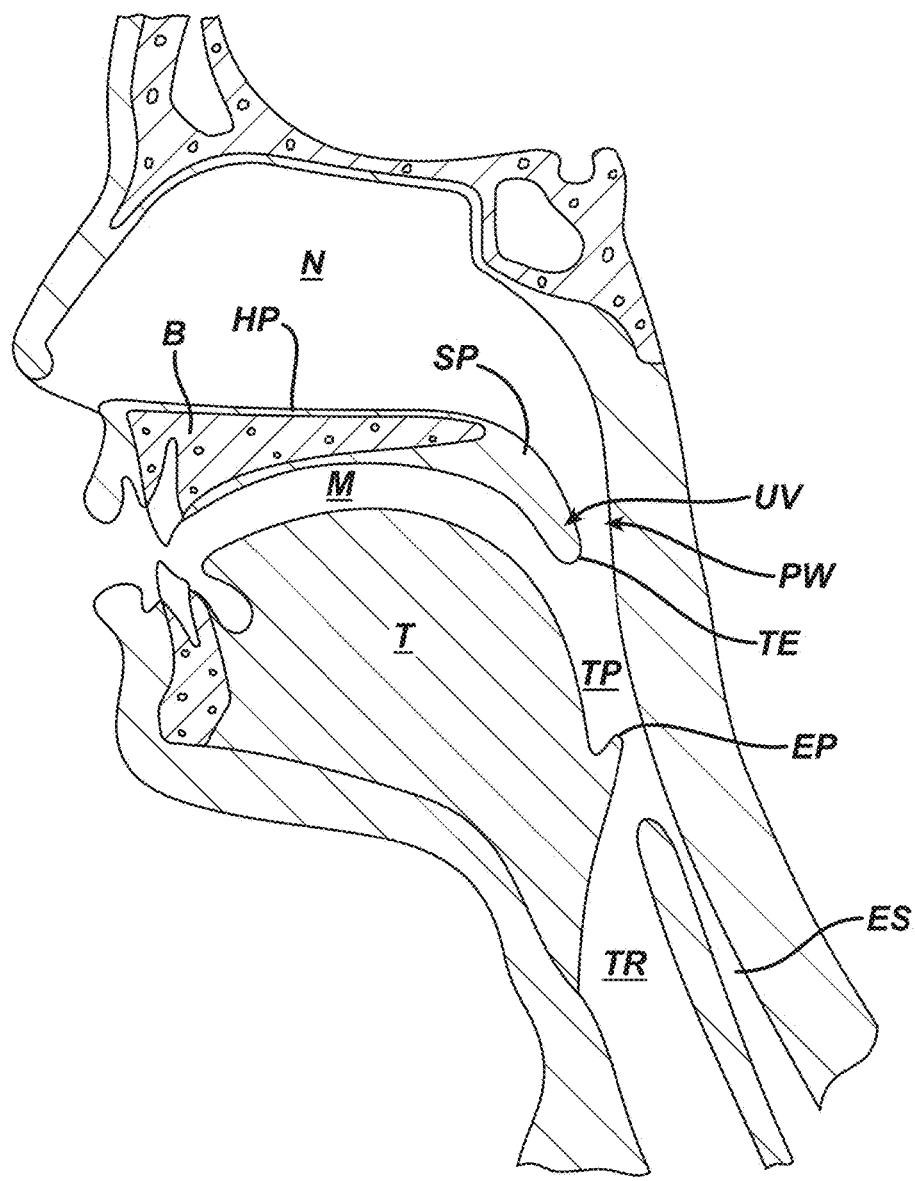
FIG. 1 is a side sectional view of a portion of a human head showing the tongue, soft palate, and other anatomical features that comprise the human airway.
Figure 2A:
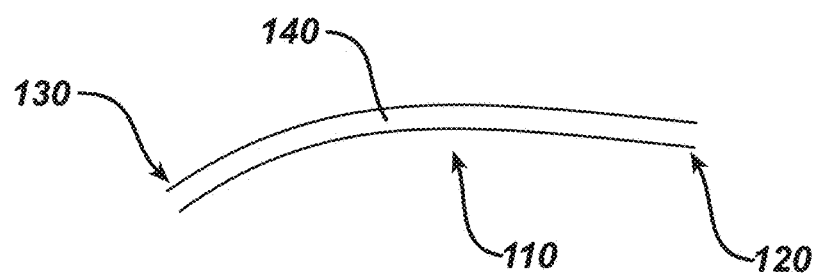
FIG. 2a illustrates the insert member.
Figure 2B:
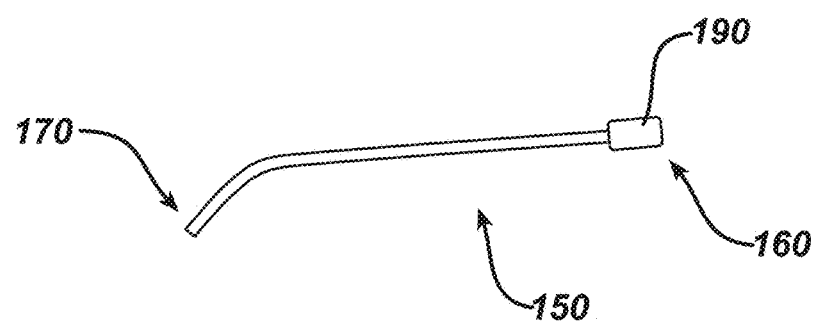
FIG. 2b illustrates the shaping member.
Figure 2C:
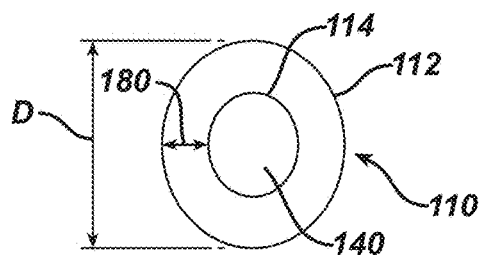
FIG. 2c illustrates a cross-section of the insert member depicting the lumen and wall thickness.
Figure 2D:
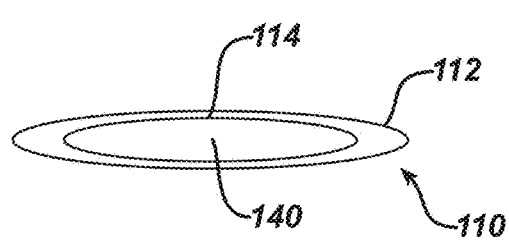
FIG. 2d illustrates a cross-section of the insert member in a collapsed state.
Figure 2E:
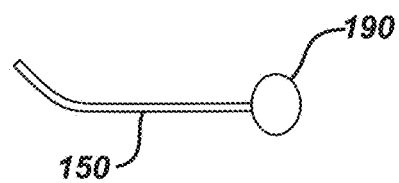
FIG. 2e illustrates the shaping member having a grip in the shape of a sphere.
Figure 2F:
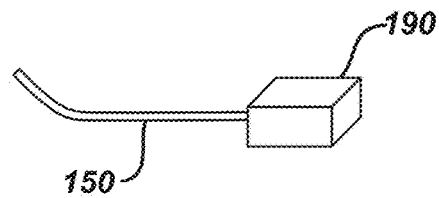
FIG. 2f illustrates the shaping member having a grip in the form of a tab.
Figure 2G:
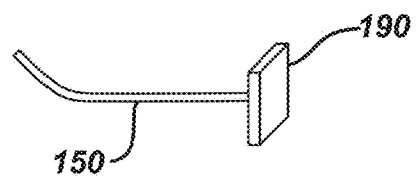
FIG. 2g illustrates the shaping member having a grip in the form of a flat tab.
Figure 2H:
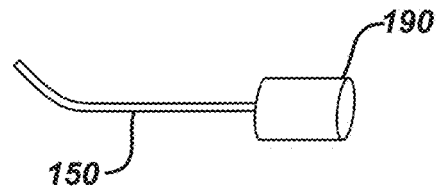
FIG. 2h illustrates the shaping member having a grip in the shape of a cylinder.

Disclosed herein is a device and method for treating Obstructive Sleep Apnea (OSA). As depicted in FIG. 2a, the device 100 is comprised of an insert member 110 having a proximal end 120 and a distal end 130 and a lumen 140 there between. A shaping member 150 having a proximal end 160 and a distal end 170 is shown in FIG. 2b wherein the 140 lumen is adapted to receive at least a portion of the shaping member 150. The shaping member 150 shown in FIG. 2b depicts an optional grip 190 at the proximal end 160. The distal end 170 can also have an optional grip 190, although not shown in FIG. 2b. The insert member 110 and the shaping member 150 work together to change or control the shape of a patient's tongue during sleep. In one embodiment, the insert member 110 has a lumen 140 that is collapsible, i.e., the lumen 140 is collapsed by the surrounding tongue tissue when the insert member 110 is placed within the tongue. FIG. 2c illustrates a cross-section of an insert member 110 depicting the lumen 140 and wall thickness 180. FIG. 2d illustrates a cross-section of the insert member 110 in a collapsed state. FIGS. 2c and 2d further illustrate the inner 114 and outer 112 surfaces of the insert member 110.

The grip 190 can be used by the patient to hold and insert the shaping member 150, and also to prevent the shaping member 150 from sliding too far into the insert member 110. In addition, the grip 190 helps to prevent saliva and food particles from entering lumen 140. Referring to FIGS. 2e-2h, the grip 190 can be a sphere (FIG. 2e), a tab (FIG. 2f), a flat tab perpendicular to the insert member 110 (FIG. 2g), a cylinder (FIG. 2h), an ellipsoid, a donut shape, or any other suitable shape. The size of the grip 190 is larger than the size of the lumen 140. The dimensions of the grip 190 are selected so that the grip 190 is more readily accessed by the patient or physician. The grip 190 is made of metal, polymeric materials, composite material, or it can be an enlarged extension of shaping member 150 and thus made of the same material as the shaping member 150.

Figure 3:
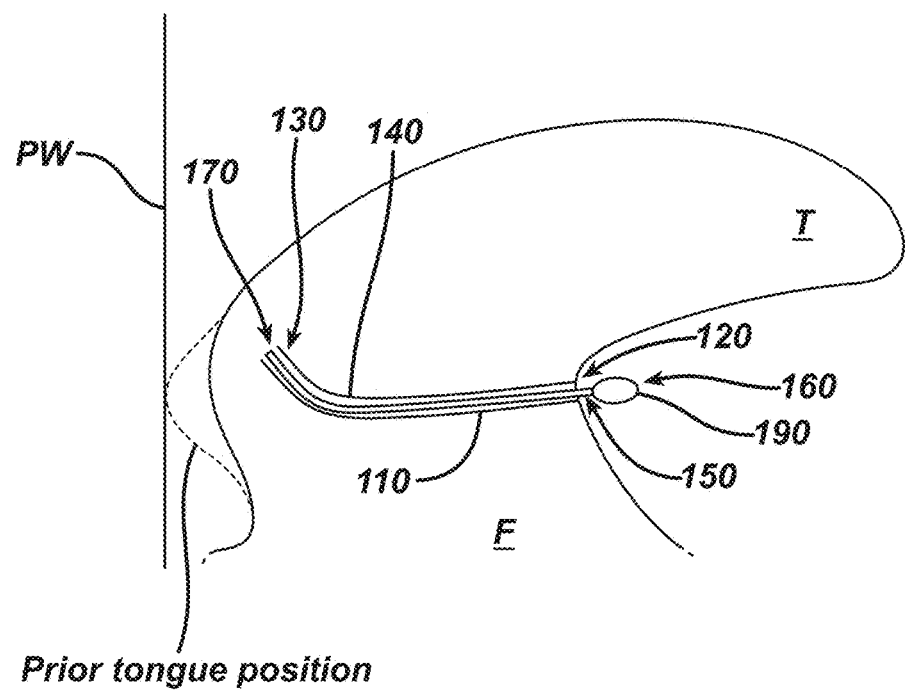
FIG. 3 illustrates the shaping member inserted into the insert member, which has been placed inside the tongue.
Figure 4A:
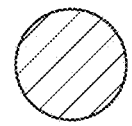
FIG. 4a illustrates a shaping member having a cross-sectional shape that is circular.
Figure 4B:
FIG. 4b illustrates a shaping member having a cross-sectional shape that is elliptical.
Figure 4C:
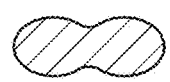
FIG. 4c illustrates a shaping member having a cross-sectional shape that is figure "8" shaped.
Figure 4D:
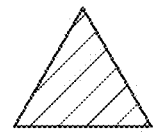
FIG. 4d illustrates a shaping member having a cross-sectional shape that is triangular.
Figure 4E:
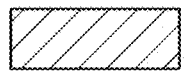
FIG. 4e illustrates a shaping member having a cross-sectional shape that is rectangular.
Figure 4F:
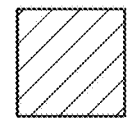
FIG. 4f illustrates a shaping member having a cross-sectional shape that is square.
Figure 4G:
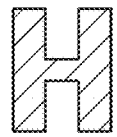
FIG. 4g illustrates a shaping member having a cross-sectional shape that is "H"-shaped.
Figure 4H:
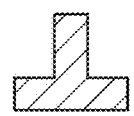
FIG. 4h illustrates a shaping member having a cross-sectional shape that is "T"-shaped.

The lumen 140 of the insert member 110 is adapted to accommodate insertion of the shaping member 150. In one embodiment, the insert member 110 is collapsible after being placed in the tongue. In another embodiment, the surface of the lumen 140 of the insert member 110 is smooth and non-porous. When there is no shaping member 150 within the lumen 140 of the collapsible insert member 110, the compliance of the insert member 110 should match that of the tissue into which it is inserted. Suitable tissues include the soft palate SP, tongue T, and pharyngeal wall PW. In some embodiments, the purpose of the shaping member 150 is to alter the shape or compliance of the tongue T, particularly near the base of tongue T, so as to reduce the degree of contact with the pharyngeal wall PW, as depicted in FIG. 3.

Referring to FIG. 4a-4h, the shaping member 150 can have a cross-sectional shape that is circular, elliptical, figure "8" shaped, triangular, rectangular, square, "H"-shaped, or "T"-shaped, respectively. In certain embodiments, the shaping member 150 cross-section corresponds to the lumen 140 of insert member 110, such as a lumen 140 with an elliptical cross-section used with a shaping member 150 with an elliptical cross-section. In certain embodiments, the shaping member 150 cross-section does not correspond to the lumen 140 of insert member 110, such as a lumen 140 with an elliptical cross-section used with a shaping member 150 with a circular cross-section.

The shaping member 150 may also have a range of stiffness to accommodate varying tissues and patient anatomy. By defining stiffness as force divided by displacement caused by said force over a length of the shaping member 150, the range of stiffness is from about 0.001 or lower to about 10 Newton per meter. The stiffness can also vary along the length of the shaping member 150, within the same ranges as described above. In one embodiment, the distal end 170 can be stiffer than the proximal end 160. In another embodiment the proximal end 160 can be stiffer than the distal end 170, depending on patient's anatomy and comfort with the device 100.

Figure 5A:
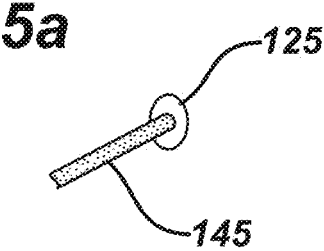
FIG. 5a illustrates the outer surface of the insert member textured with texture.
Figure 5B:
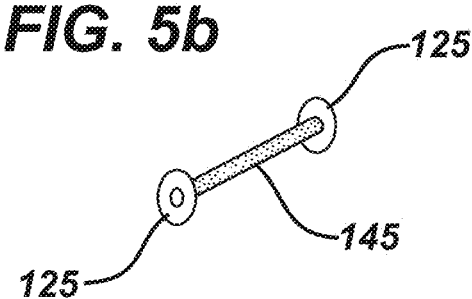
FIG. 5b illustrates the outer surface of the insert member textured with texture.

In one embodiment, the outer surface 112 of the insert member 110 is smooth, allowing for easy exchange or removal from the tongue. In another embodiment, the outer surface 112 of the insert member 110 is optionally textured with texture 145 as shown in FIGS. 5a and 5b. In this embodiment, tissue ingrowth can be induced to secure the insert member 110 within the tongue T by roughening the outer surface 112 of the insert member 110 by any of the known techniques (laser etched, chemical etched, mechanical treatment, or imparted during extrusion) to impart knurled surface, pitted surface, ridged surface, etc. The outer surface 112 of the insert member 110 may also be wrapped by a textile, such as polyethylene terephthalate or polytetrafluoroethylene, to impart a rougher textured surface for interaction with the tissue or to facilitate tissue attachment.

Figure 6:
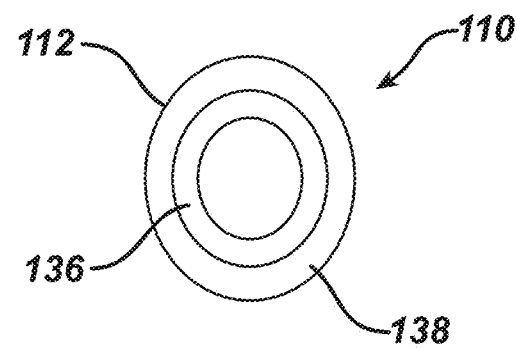
FIG. 6 illustrates an embodiment with the insert member comprising a coaxially disposed inner layer and an outer layer.

In one embodiment the insert member 110 is comprised of two layers of dissimilar polymers coaxially disposed, with layers being from 1-500 microns, more typically from 25 to 500 microns. The layers are applied by any method known in the art, such as spray, shrink wrap, co-extrusion, mechanical joining with optional adhesive reinforcement, etc. The polymers are any biocompatible polymers, including, for example, PET, PTFE, polypropylene, as well as resorbable polymers, such as PLGA, PGA, PLA, PDS, or similar. FIG. 6 shows an embodiment with the insert member 110 comprising a coaxially disposed inner layer 136 and an outer layer 138. In another embodiment, the outer layer 138 can be a textile that has been glued or welded to the inner layer 136.

Figure 7A:
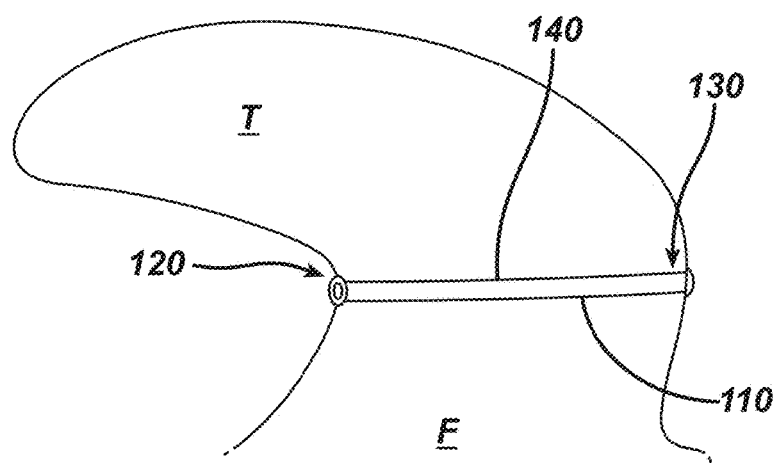
FIG. 7a illustrates an insert member placed completely through the tongue.
Figure 7B:
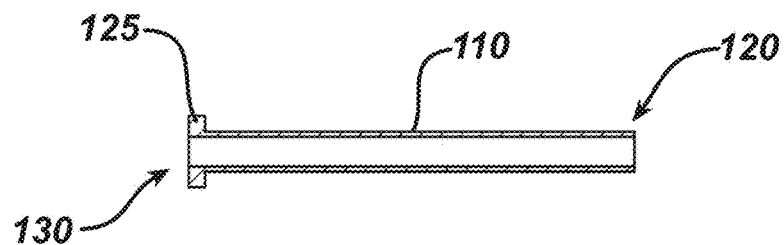
FIG. 7b illustrates the insert member having flange on the distal end.
Figure 7C:
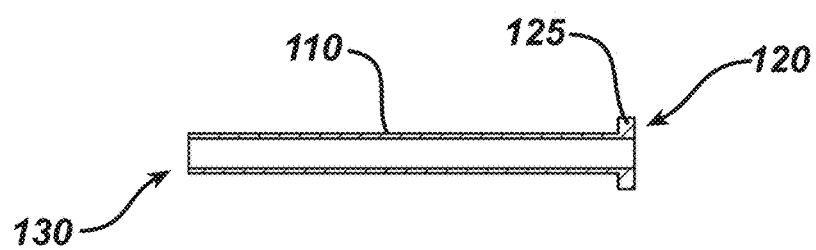
FIG. 7c illustrates the insert member having flange on the proximal end.
Figure 7D:
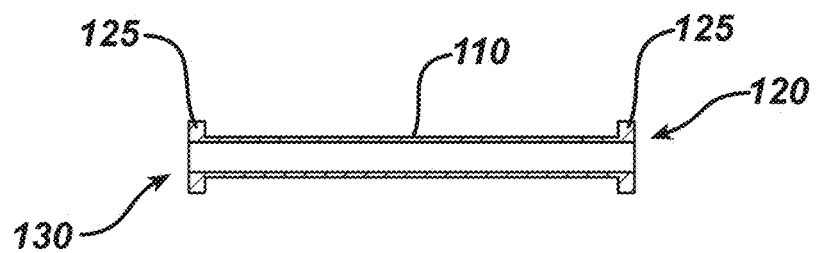
FIG. 7d illustrates the insert member having flanges on both the proximal and distal ends.

In one embodiment, the insert member 110 can be placed all the way through the tongue T, e.g., from the frenulum F to the base of tongue as shown in FIG. 7a. In this through-tongue embodiment, the proximal 120 and/or distal 130 ends of the insert member 110 may have flanges 125 as shown in FIGS. 7b, 7c, and 7d, with flanges 125 on the distal end 130 (FIG. 7b), on the proximal end 120 (FIG. 7c), or both proximal 120 and distal 130 ends (FIG. 7d) of the insert member 110 to help secure the ends of the insert member 110 in the tongue T. The flanges 125 are made of metal, polymeric materials, composite material, or it can be an enlarged extension of insert member 110 and thus made of the same material.

In another embodiment, the proximal end 160 of the shaping member 150 is adapted to be positioned near the proximal end 120 of the insert member 110.

Figure 8:
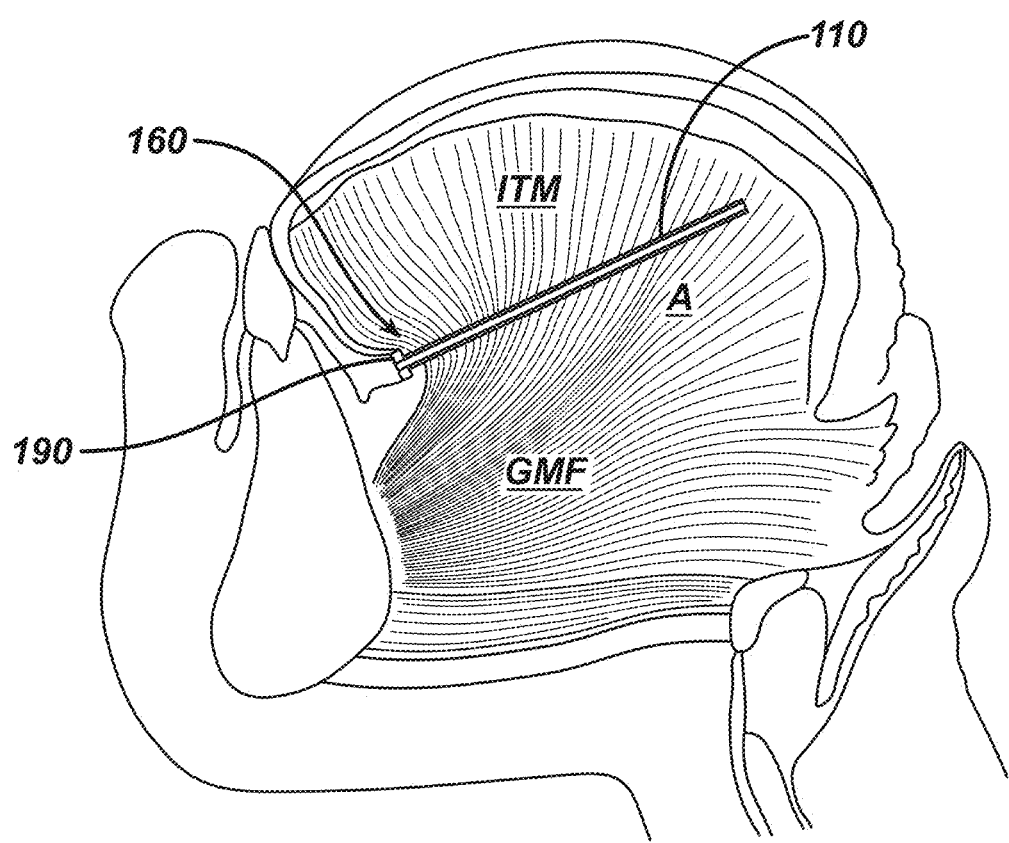
FIG. 8 illustrates an intra-tongue position of the insert member wherein the insert member does not pass completely through the tongue.

In yet another embodiment, the collapsible insert member 110 may also be placed within the tongue T, e.g., from the frenulum F to the point in the tongue T where the genioglossus muscle fibers GMF engage the intrinsic tongue musculature ITM, in the area A as shown in FIG. 8. In one embodiment of this intra-tongue device positioning, the proximal end 160 of the shaping member 150 (near the frenulum mucosa FM) could have grip 190. In one embodiment, the distal end 130 of the insert member 110 may house a magnet or hook that may engage the distal end 170 of the shaping member 150, provided the shaping member 150 has a magnet or hook placed thereon. This would ensure placement of the distal end 170 of the shaping member 150 meets the distal end 120 of the insert member 110. It may also serve as a mechanism for pulling the tongue base anteriorly.

In another embodiment, the shaping member 150 is produced from a shape memory material, such as nitinol, that has been heat treated or trained to facilitate easier installation by the patient prior to sleep. The transformation temperature of the shaping member 150 is set to be slightly lower than body temperature to facilitate the transition of the structure from the martensitic to austenitic state. The shaping member 150 is chilled to a temperature while placed within a holder in preparation to allow the shaping member 150 to maintain a straightened shape once removed from the holder and during the insertion. The chilled shaping member 150 is then allowed to warm up to room temperature or 20-25 degrees Celsius and is then inserted within the insert member 110 in the straightened configuration. As the shaping member 150 warms up to body temperature, the geometry of the shaping member 150 resumes its trained condition of being non-straight shaped. Upon resumption of the "trained shape", the device 100 (shaping member 150 and insert member 110) applies a force to the tissues of the tongue to cause a repositioning or re-shaping of the tongue. Through the utilization of the temperature effect, the device 100 can be set to provide significant re-shaping of the tongue without difficulty during installation by the patient.

In one embodiment, the shaping member 150 is telescopic, i.e., a series of concentric segments can be deployed to various distances in the lumen 140 of the insert member 110. The shaping member 150 can induce the tongue to deflect anteriorly, posteriorly, to the left, to the right, or combinations thereof. In another embodiment, two or more separate insert members can be placed at various sites in the tongue, each to receive separate shaping members that alter the tongue shape or compliance differently.

In an additional embodiment, the shaping member 150 is constructed as a bimetallic bonded strip that is contained within a flexible elastomeric sheath manufactured from or coated with a flexible material such as silastic, rubber, or elastomeric polymers such as polyesters, polyurethanes, polyethylene, or other polyolefins. The coating or wrapping material is provided to protect the bimetallic bonded strips from oral secretions and to facilitate cleaning of the shaping member after use.

The bimetallic strip is constructed from strips of two dissimilar materials with differing coefficients of thermal expansion that are assembled together along the long axis of the two strip materials through the use of welding or other mechanical means such as rivets, adhesives, interlocking features, etc. Suitable materials include steel, copper, aluminum, or any other flexible metallic material. The strip is constructed with the two lengths of dissimilar material fixed together in a straightened condition at a particular temperature, such as room temperature. Once the shaping member 150 is heated from the chilled temperature to body temperature, the shaping member 150 bends to accommodate the differing expansion rates of the two materials utilized in the bonded bimetallic shaping member 150. As the shaping member is heated to body temperature, it bends to accommodate the different thermal expansion rates of the two materials. Since the shaping member is fabricated in the straightened condition at room temperature, it enables the placement of the shaping member in a straightened configuration within the lumen 140 of the insert member 110 and subsequently provides necessary reshaping of the tongue as the shaping member 150 achieves room temperature and subsequently bends in response to the differing coefficients of thermal expansion of the two metallic materials utilized in the shaping element.

In one embodiment, as shown in FIGS. 9a and 9b, two or more insert members 110 can be placed in the tongue T to provide better stability on two sides of the tongue or to provide differentiated stiffening on two sides of the tongue, which can be helpful for a very large tongue. In one embodiment, the two insert members 110 are connected along the whole length. In another embodiment, the two insert members 110 are connected only at the proximal ends 120 thus forming a Y-shape as shown in FIGS. 9a and 9b. In one embodiment, two shaping members 150 are utilized. In another embodiment, two shaping members 150 are connected at the proximal ends. In these embodiments, devices can be installed intra-tongue (as shown in FIG. 9a) or through-tongue (as shown in FIG. 9b) (similar to FIGS. 7a and 8).

In another embodiment, the shaping member 150 for deployment as an intra-tongue device has a tensioning element in it, wherein the tensioning element contains a hook, a magnet, or a spring. This embodiment is fabricated as a multi-component device.

Figure 10A:
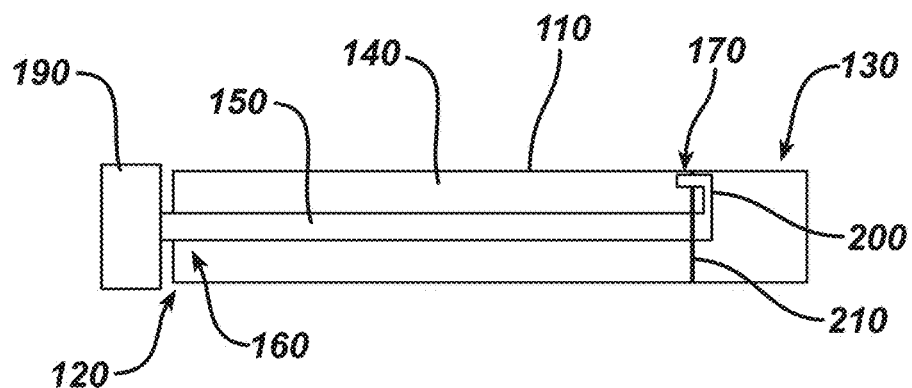
FIG. 10a illustrates an embodiment of the invention wherein the shaping member has a hook disposed on the distal end of shaping member, and the insert member has a cross-bar on the distal end of the insert member for attachment of the hook.

In one embodiment, the shaping member 150 has a hook 200 disposed on distal end 170 of shaping member 150, with the insert member 110 having a feature, such as a cross-bar 210, on the distal end 130 for attachment of the hook 200. As shown in FIG. 10a, the hook 200 is engaged with a cross-bar 210 disposed within the lumen 140 of the insert member 110 at the distal end 130.

Figure 10B:
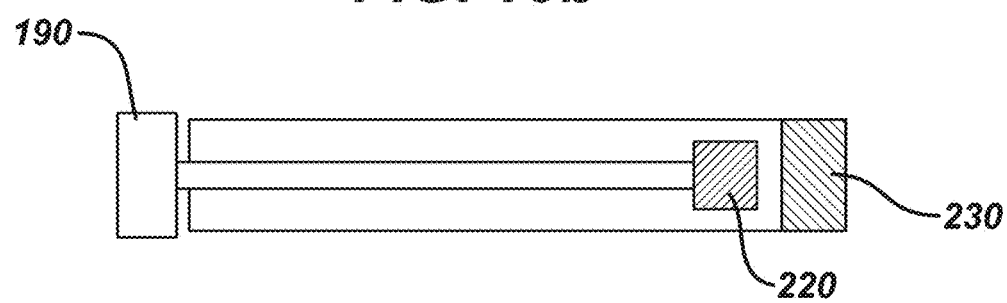
FIG. 10b illustrates an embodiment of the invention wherein the shaping member has a magnet disposed on the distal end of shaping member, and the insert member has a magnet on the distal end of the insert member for attachment of the hook.

In another embodiment, the shaping member 150 has a magnet 220 disposed on distal end 170 of shaping member 150, with the insert member 110 having a magnet 230 or another ferromagnetic material on distal end 130 for engaging the distal end 170 of the shaping member 150. As shown in FIG. 10b, the magnet 220 at the distal end 170 of the shaping member 150 is engaged with the magnet 230 or other magnetic material of the insert member 110 at the distal end 130.

Figure 10C:
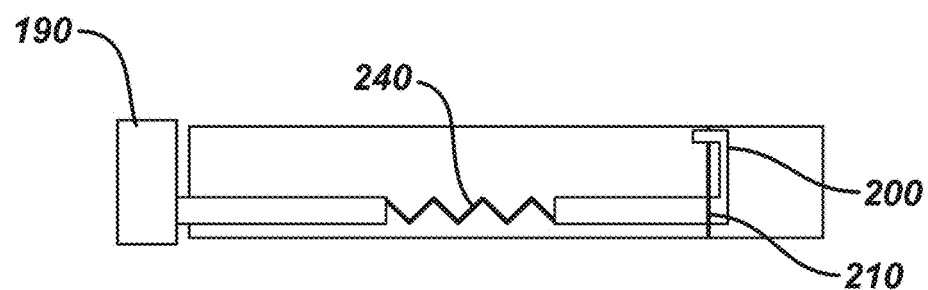
FIG. 10c illustrates an embodiment of the invention wherein the shaping member has a hook disposed on the distal end of shaping member and a spring element disposed between the distal and proximal ends of the shaping member, and the insert member has a cross-bar on the distal end of the insert member for attachment of the hook.

In another embodiment, the shaping member 150 has a hook 200 disposed on distal end 170 of the shaping member 150 and a spring element 240 disposed between the distal 170 and proximal 160 ends of shaping member 150. The spring element 240 enables better fixation of the shaping member 150 as well as provides shaping properties, damping properties, tightening properties, and flexibility. The spring element 240 is made from any suitable material such as metal or metal alloy by wire processing or any other process known in the art. Referring to FIG. 10c, the hook 200 is engaged with a cross-bar 210 disposed within the lumen 140 of the insert member 110 at the distal end 130 of the insert member 110.

Figure 11B:
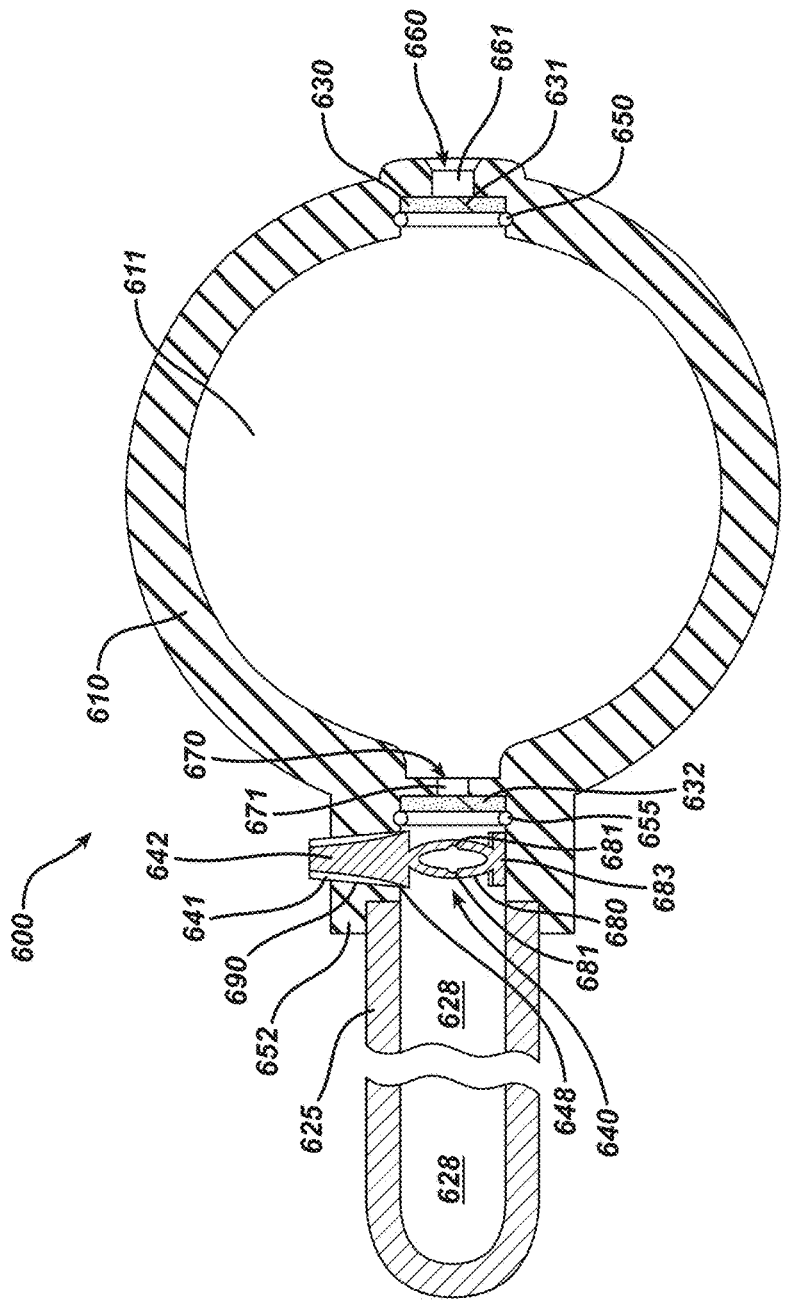
FIG. 11b illustrates a cross-sectional view of the bulb assembly.

An alternative embodiment of the shaping member is illustrated in FIGS. 11a-11f. Referring to FIGS. 11a-11f, the shaping member is a flexible hollow device that is altered in shape through the use of fluid pressurization. FIG. 11b is a cross sectional view of the shaping member. As shown in FIG. 11a, the shaping member 601 is comprised of a bulb assembly 600 and a hollow pressure receiver chamber 625. The bulb assembly 600 serves the additional function of providing the necessary grip feature, similar to the grip 190 illustrated in FIG. 2b, of the shaping member 601. The bulb assembly 600 is comprised of a flexible bulb 610 with two internal, elastomeric, one way valves 630 and 632, two mechanical lock rings 650 and 655, and an external relief valve 640. The bulb assembly 600 is attached to the hollow pressure receiver chamber 625. The pressure receiver chamber 625 is sealed at one end and is in fluid communication with the hollow inner chamber 611 of the flexible bulb 610. The pressure receiver chamber 625 is intended to receive the fluid medium from within the inner chamber 611 of the flexible bulb 610.

The flexible bulb 610 is formed from an elastomeric material selected from groups including silastics, latex rubber, natural rubbers, polyurethanes, polyethylenes, polyolefins, polyesters, etc. The flexible bulb 610 is generally spherical in shape and comprises a hollow inner chamber 611 (see FIG. 11b). Ports 660 and 670 are formed in the opposing ends of the flexible bulb 610. The proximal 660 and distal 670 ports enable fluid communication into and out of the flexible bulb 610 during compression and release of the bulb assembly 600. In the embodiment, two elastomeric one way valves 630 and 632 are located in abutment to each port 660 and 670.

Figure 11D:
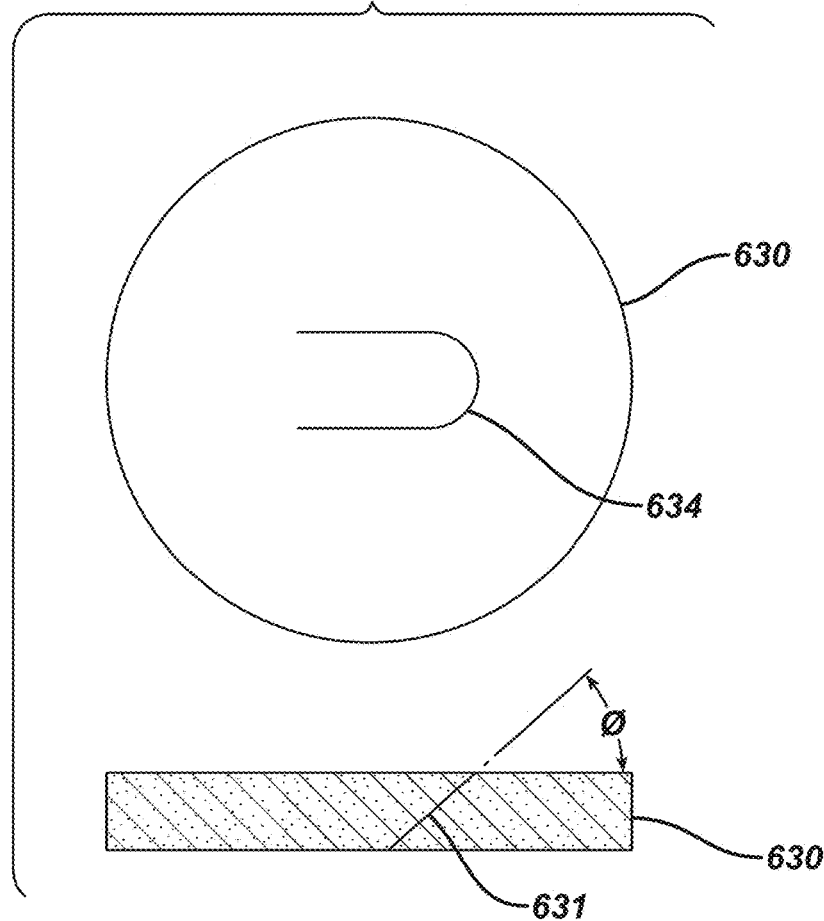
FIG. 11d illustrates a top view and a cross-sectional view of an internal, elastomeric, one way valve located in the flexible bulb of the bulb assembly comprising a curvilinear slit that forms a flap through the one way valve.
Figure 11E:
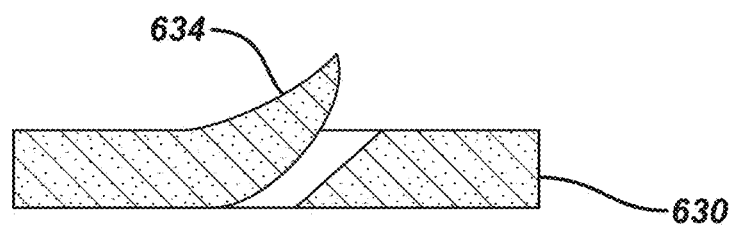
FIG. 11e illustrates the flap formed from the curvilinear slit through the one way valve.

Referring to FIGS. 11d and 11e, the first 630 and second 632 elastomeric one way valves are fabricated as short cylinders. The short cylinders are formed through the use of hollow circular punches that punch out the short cylinders from a sheet of elastomeric material such as silastic.

Curvilinear slits are cut through the flat surfaces of the cylinders at an angle Theta thereby forming flaps through the first 630 and second 632 one way valves. As depicted in FIGS. 11d and 11e, a first 631 curvilinear slit is cut through the flat surface of the cylinder at an angle Theta thereby forming first flap 634 through the first one way valve 630. The first 630 and second 632 elastomeric one way valves may be bonded to the inner surface of the proximal 660 and distal 670 ports, respectively, through the use of adhesives, solvents, or welding, or may utilize a mechanical retention devices such as the lock rings 650 and 655 illustrated in FIG. 11b.

As the curvilinear slit 631 has been cut at an angle Theta through the short cylinder of elastomeric material, flap 634 that is formed will be self-sealing when pressure is applied against the side of the first elastomeric one way valve 630 where the first curvilinear slit 631 was initiated. First 630 and second 632 elastomeric one way valves are installed within the lumens 661 and 671 of the proximal 660 and distal 670 ports, respectively. The first valve 630 is installed on the proximal port 660 of the hollow inner chamber 611 of the flexible bulb 610 with the first curvilinear slit 631 initiated side of the first elastomeric one way valve 630 facing distally, or towards the inner chamber 611 of the flexible bulb 610. In this orientation, the flap may bend towards the inner chamber 611 of the flexible bulb 610 to open; however, it resists motion in the proximal direction 636 towards the proximal port 660 and remains sealed. This orientation enables fluid communication from the atmosphere, or an external source of fluid, into the inner chamber 611 of the flexible bulb 610 when the flexible bulb 610 is released from a compressed or collapsed condition.

The second elastomeric one way valve 632 is installed within the distal port 670 of the flexible bulb 610. The second elastomeric one way valve 632 is installed with the second curvilinear slit 633 initiated surface facing distally, or towards the hollow pressure receiver chamber 625. With the second elastomeric one way valve 632 in this orientation, the second flap 635 may move distally to open towards the hollow pressure receiver chamber 625; however, it will resist motion in the proximal direction or the direction of the inner chamber 611 of the flexible bulb 610. In this orientation, the second elastomeric one way valve 632 allows fluid communication from the inner chamber 611 of the flexible bulb 610 when the flexible bulb 610 is pressurized; however, the second elastomeric one way valve 632 prevents fluid communication when the pressure in the hollow pressure receiver chamber 625 is greater than the pressure within the inner chamber 611 of the flexible bulb 610. The second elastomeric one way valve 632 is held in engagement with the port 670 of the flexible bulb 610 through the use of the mechanical lock ring 655.

Figure 11F:
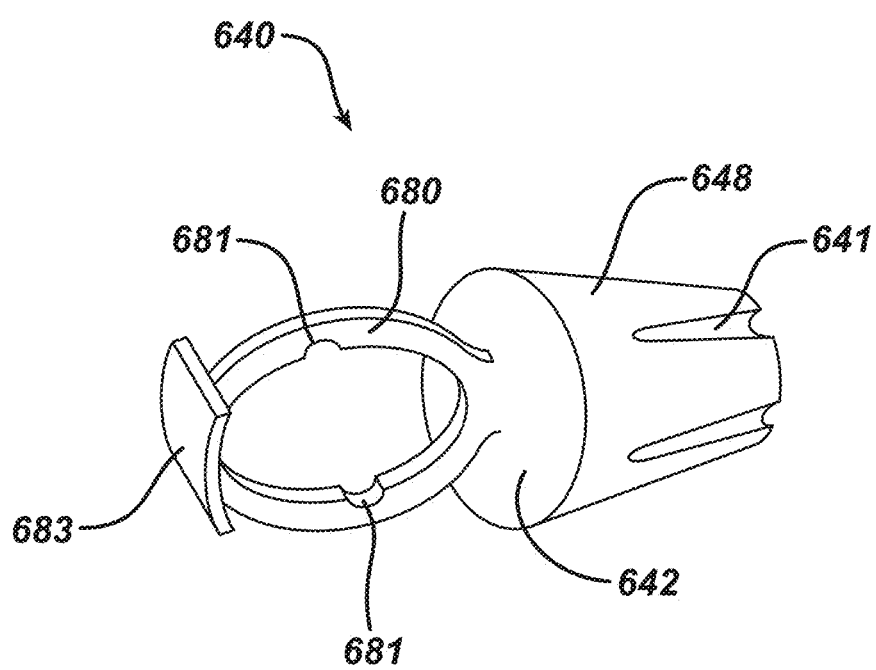
FIG. 11f illustrates an external relief valve of the shaping member depicted in FIG. 11b.

The shaping member 601 includes an externally venting pressure relief valve 640, comprised of any biocompatible polymeric material known to those skilled in the art, in communication with the lumen 628 of the pressure receiver chamber 625. As shown in FIGS. 11b and 11f, the valve 640 is fabricated with a tapered sealing surface 648 that is received within a tapered passage 690 formed through the distal side wall 652 of the flexible bulb 610. The pressure relief valve 640 is formed with tapered depth channels 641 formed about the perimeter of the tapered sealing surface 648. The pressure relief valve 640 is maintained in the sealed position through the use of a spring mechanism. Suitable spring mechanisms include coil springs, tension springs, elastomeric foam structures, or integral spring features. In another embodiment, the pressure relief valve 640 is formed with an integral flexible ring structure 680 extending between the valve stem 642 and the valve base 683. The integral flexible ring 680 is produced with two opposing thin walled sections 681. The two thin wall sections are approximately 30 percent of the thickness of the balance of the integral flexible ring 680. The thin wall sections 681 serve as hinge features that increase the flexibility of the integral flexible ring. When the relief valve 640 is depressed by the patient, the integral flexible ring 680 flexes and the hinge structures or thin wall sections 681 enable the buckling of the integral flexible ring 680 with a reduced force. This flexure and buckling of the integral flexible ring 680 enables the tapered depth channels 641 to be displaced into the pressure receiver chamber lumen 628. This motion of the tapered depth channels 641 enables fluid communication of the lumen of the pressure receiver chamber 628 with the surrounding atmosphere to release the pressure through the escape of pressurized fluid along the tapered depth channels 641.

The pressure receiver chamber 625 portion of the shaping member 601 may be fabricated as a single lumen device that has a pre-determined, curved geometry. Alternatively the pressure receiver chamber portion 625 of the shaping member 601 may be fabricated as a non-symmetrical hollow chamber with varying wall geometry. In one non-symmetric embodiment, as shown in FIG. 11*a*, the pressure receiver chamber 625 is formed with a generally straight wall configuration 622 parallel to the center axis line of the pressure receiver chamber. The opposing half of the chamber wall is formed with a corrugated or undulating side wall 621. In the absence of elevated pressure within the pressure receiver chamber 625, the pressure receiver chamber 625 is a semi-flexible structure, with a generally straight form capable of being passed within an insert member located within the tongue. Once the pressure receiver chamber 625 portion of the shaping member 601 is positioned within the tongue, the flexible bulb 610 is compressed by the patient and the pressure receiver chamber 625 becomes pressurized. Repeated compression and release cycles of the flexible bulb 610 serve to increase the pressure within the pressure receiver chamber 625 thereby causing stiffening and shape alteration. Referring to FIG. 11*c*, pressurization of the non-symmetrical pressure receiver chamber 625 is illustrated, wherein P1 represents the initial fluid pressure within the lumen 628 of the pressure receiver chamber 625, and P2 represents the pressure of the fluid within the lumen 628 of the pressure receiver chamber 625 after pressurization and is greater than P1. The increase in pressure causes the pressure receiver chamber 625 shape to be altered into a curved or bent configuration.

Figure 12A:
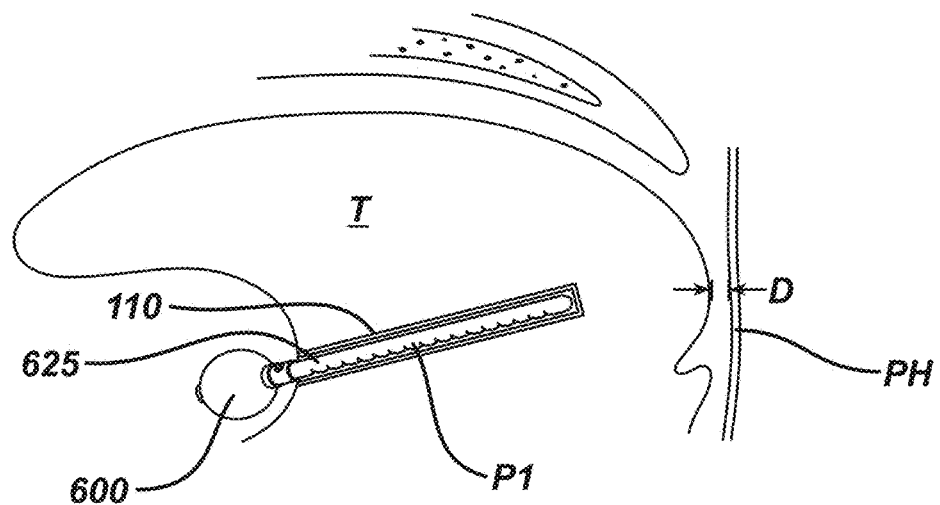
FIG. 12a illustrates the shaping member illustrated in FIGS. 11a-f installed within an insert member in the tongue.
Figure 12B:
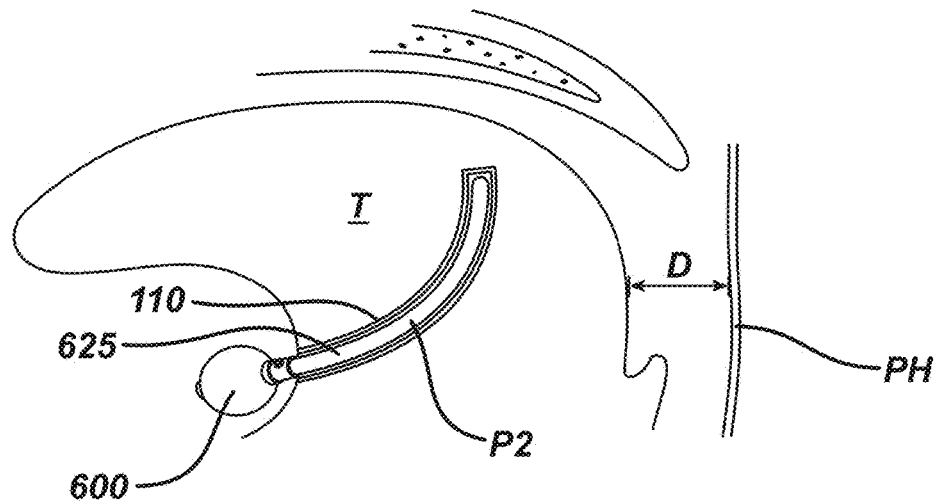
FIG. 12b illustrates that as the pressure increases within the pressure receiver chamber of the shaping member, the shaping member becomes non-straight.
Figure 13:
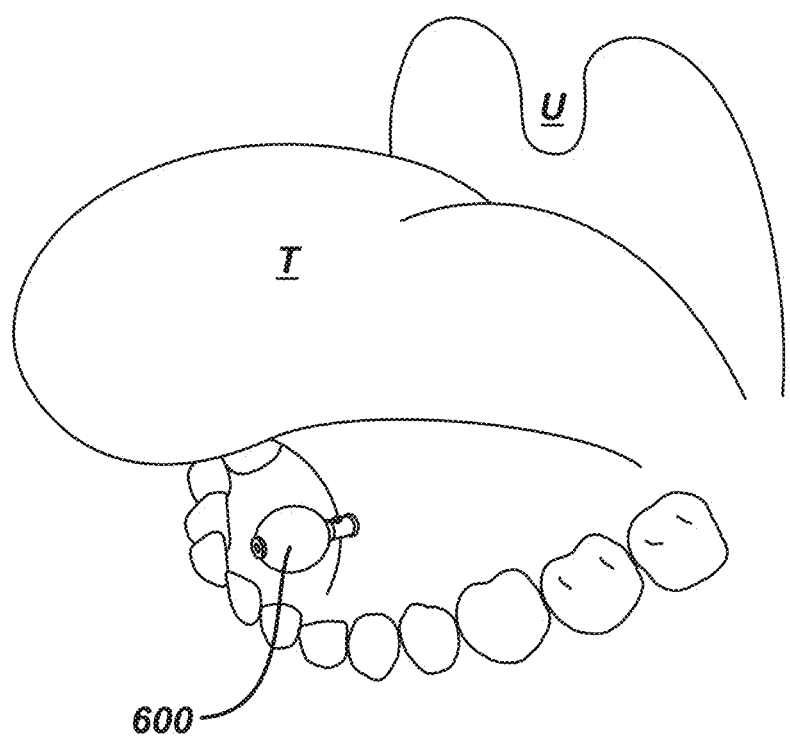
FIG. 13 illustrates that upon completion of the installation of the pressurized shaping member shown in FIGS. 11a-f and 12a-b within the lumen of the insert member, the bulb assembly portion of the shaping member remains accessible to the patient.

Referring to FIGS. 12*a* and 12*b*, when the shaping member 601 is installed within an insert member 110 in the tongue T and as the pressure increases within the pressure receiver chamber 625, the shaping member 601 becomes non-straight as the corrugated side of the pressure receiver chamber continues to elongate thereby shifting the shape or position of the tongue away from the posterior wall of the pharynx PH increasing the distance D of the tongue base from the pharynx PH. Referring to FIG. 13, it can be seen that upon completion of the installation of the pressurized shaping member 601 within the lumen 140 of the insert member 110, the bulb assembly portion 600 of the shaping member remains accessible to the patient for subsequent depressurization and removal as necessary.

The pressurized embodiment of the shaping member 601 enables the placement of the shaping member 601 within the insert member 110 in the tongue T in a straightened condition. Once installed within the insert member 110, the patient is able to adjust the shaping of the tongue T by either increasing or decreasing the pressure within the pressure receiver chamber 625 of the shaping element 601. Additionally, upon waking, the patient may easily remove the shaping member 601 from within the insert member 110 in a depressurized or straightened or flexible condition. This flexible/straightened condition eliminates the discomfort that may be associated with passing a bent shaping member 601 from within the insert member 110.

The shaping member 601 is able to provide a stiffness range to accommodate varying tissues and patient anatomy under the control of the patient. By defining stiffness as force divided by displacement caused by said force over a length of the stiffening member, the range of stiffness is from about 0.001 or lower to about 10 Newton per meter.

Figure 14A:
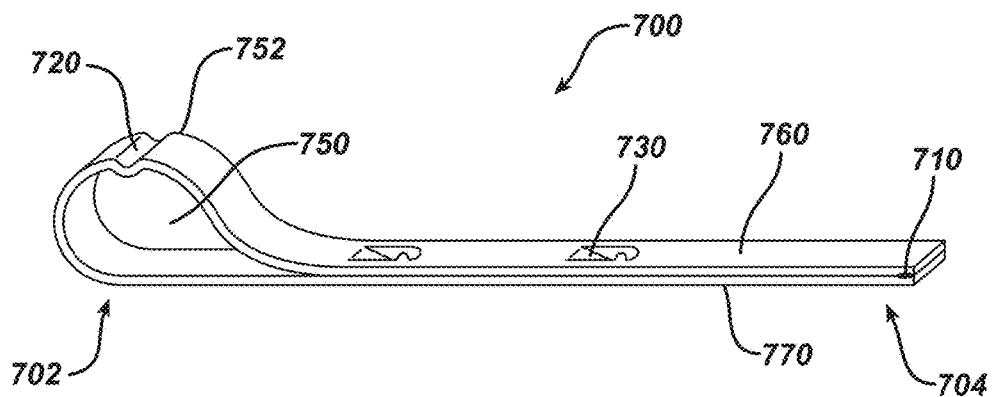
FIG. 14a illustrates an embodiment of the invention wherein the shaping member comprises a first and second leg element.

Alternative geometries of the shaping member are also contemplated. As shown in FIG. 14*a*, the shaping member 700 may be constructed from a folded ribbon or rod like structure. The folded structure forms a first leg element 760 and a second leg element 770 with a looped end 750 of the shaping member 700 that is to be grasped by the patient. The looped end 750 of the shaping member 700 is defined as the proximal end; the opposite end of the shaping member 700 is defined as the distal end of the shaping member 700. The distal ends of the two leg elements 760 and 770 of the shaping member 700 are fused together 710 through welding, gluing, or the use of mechanical fasteners such as screws, rivets, bands, etc. The proximal looped end 750 of the shaping member 700 is formed with a detent surface 720. The shaping member 700 comprises only one looped end 750 thereby forming a shape similar to the letter "P".

Figure 14B:
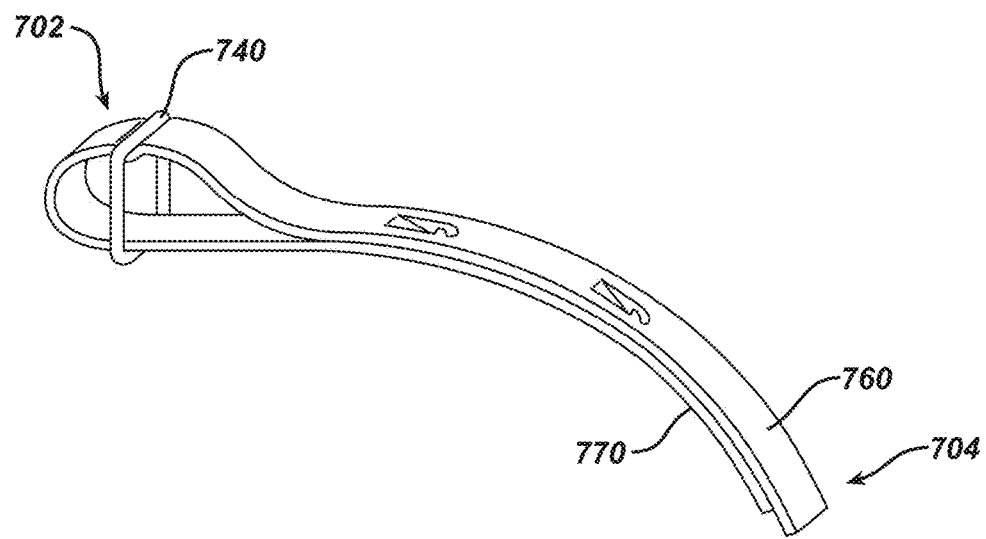
FIG. 14b illustrates an embodiment of the invention wherein the shaping member comprises a first and second leg element and locking ring.

Interlocking elements 730 are formed in the mating surfaces of the two leg elements 760 and 770. The interlocking elements 730 are simple punched geometries that are displaced from one leg into receiver slots located in the opposing leg. A locking ring 740 that is located on the proximal end of the shaping member 700 is slid over the looped end 750 of the shaping member 700 by the patient until it reaches the detent surface 720. As the locking ring 740 is passed along the length of the looped end 750 of the shaping member 700, the locking ring 740 causes compression of the looped end 750 as shown in FIG. 14*b*. Once locked into position, the deflection of the arced side 752 of the shaping member 700 causes the leg 760 to become slightly longer.

As previously described, the distal ends of the leg elements 760 and 770 are fused together 710. Similar to the bimetallic bonded strip previously described, the extension of leg 760, while the length of leg 770 is fixed due to the compression caused by the locking ring 740, results in the bending of the shaping member 700 as shown in FIG. 14*b*. As legs 760 and 770 of the shaping member 700 bend, the bending of legs 760 and 770 exerts a force to change the shape or position of the tissue. The shaping member 700 may be contained within a flexible elastomeric sheath manufactured from or is coated with a flexible material such as silastic, rubber or elastomeric polymers such as polyesters, polyurethanes, polyethylene, or other polyolefins. The coating or wrapping material is provided to protect the strip materials from oral secretions and to facilitate cleaning of the shaping member 700 after use.

The embodiment of the shaping member 700 enables the placement of the shaping member 700 within the insert member in the tongue in a straightened condition. Once installed within the insert member, the patient is able to alter the shape of the tongue by placing the locking ring 740 over the looped end 750 of the shaping member 700. Additionally, upon waking, the patient may easily remove the shaping member 700 from within the insert member in a straightened condition by removing the locking ring 740 from the looped end 750. This straightened condition eliminates the discomfort that may be associated with passing a bent shaping member 700 from within the insert member.

Materials

Insert member 110 of the device 100 for treating obstructive sleep apnea comprise polymeric tubes made by known methods of extrusion, injection molding, casting on mandrels, such as centrifugal casting, and other methods known to those skilled in the art. Materials used to make insert member 110 include any biocompatible polymers, including expanded polytetrafluoroethylene (ePTFE), silicone, polyether ether ketone (PEEK), polypropylene, polyethylene, polyethylene terephtalate, and combinations thereof. In one embodiment, the insert member 110 and shaping member are comprised of a metal or polymer or combinations thereof. In another embodiment, the metal is selected from the group consisting of nitinol, stainless steel, tantalum, and titanium. In another embodiment, the polymer is selected from the group consisting of silicone, polyethylene, polypropylene, fluoropolymers, and PEEK.

The insert member 110 may be a composite of an absorbable (such as collagen, lactide/glycolide copolymers or similar) or dissolvable polymer (polyvinyl alcohol (PVA), polyethylene glycol (PEG), or similar) and non-resorbable fibers or particulates (e.g. ePTFE, silicone, PEEK, polypropylene, polyethylene, polyethylene terephthalate, and combinations thereof). In this embodiment, the absorbable portion of the insert member 110 provides a temporary interface within which the shaping member may be passed. As the dissolvable material is removed from the site, the non-resorbable material serves as a stimulant for the maintenance of the tubular scar tissue. This tubular scar tissue serves as the permanent lumen to receive the shaping member. Longer-term, the use of the resorbable or dissolvable material obviates the need to remove any physical implant in the case of reversibility. The lumen or channel formed in the tongue of the scar tissue needs only be scraped or debrided and temporarily held together to facilitate closure of the lumen or channel in the tongue formed by the scar tissue.

The shaping member can be made from nitinol, stainless steel, polymer, piezoelectric materials, magnetic or rheomagnetic materials, or any other known biocompatible implant material capable of providing a change in the tissue response to stress. The shaping member has a proximal end that is exposed in the frenulum. This end may be a bulb or cylinder or hook that can easily be grasped by the patient so that they can insert it prior to sleep and remove it upon waking. In order to reduce accumulation of fluid or food in the lumen of the insert member during the day, a shaping member with a compliance matching that of the relaxed tongue can be optionally inserted into the insert member 110 lumen 140 during the day.

The shaping member 700 may be made from polymeric or metallic materials. Suitable non-absorbable materials for use in the present invention include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) Poly (hexafluoropropylene-VDF), polyaryletherketones, polyolefins (e.g. polypropylene including isotactic and syndiotactic polypropylene and blends thereof, as well as, blends composed predominately of isotactic or syndiotactic polypropylene blended with heterotactic polypropylene and/or polyethylene (such as is described in U.S. Pat. No. 4,557,264 issued Dec. 10, 1985, assigned to Ethicon, Inc., hereby incorporated by reference in its entirety) and combinations thereof. Stainless Steel and Nitinol.

In another embodiment, the insert member 110 or shaping member are further comprised of an antimicrobial agent. The agent can be a coating on insert member 110 or shaping member or impregnated within the polymer of construction. The agent can be selected from the group of triclosan, chlorhexidine gluconate, silver, copper, polyhexamethylene biguanide (PHMB), antibiotics, and other agents having antimicrobial activity.

In certain embodiments, insert member 110 has a diameter D (as shown in FIG. 2c) from 0.5 mm to 5 mm, and length from about 20 mm to about 60 mm, with wall thickness from about 100 microns to about 2 mm. The wall thickness can vary within the insert member 110 from proximal end 120 to distal end 130 so that compliance or flexibility is variable along the length of insert member 110. Wall thickness 180 also can vary along the circumference as seen in FIG. 2d to enable conformation and compliance matching to the patient's tongue and shaping member. The materials and dimensions described above are selected so as to ensure that compliance of insert member 110 matches the tongue and surrounding tissue so that the patient feels minimal discomfort. In some embodiments the insert member has a flat or elliptical profile in cross-section as shown schematically in FIG. 2d.

In certain embodiments, the shaping member has a diameter from 0.1 mm to 4 mm, and length from about 20 mm to about 60 mm. In non-circular cross-sections, the dimensions can vary from 0.2 mm×4 mm to 2 mm×3 mm. The diameter can vary within the shaping member from proximal end to distal end so that compliance or flexibility is variable along the length of shaping member. The cross-sectional shape can also vary within the shaping member from proximal end to distal end so that compliance or flexibility is variable along the length of shaping member. In one embodiment, the cross-sectional shape at the proximal end 160 is circular (FIG. 4a), and changes to an "H"-shaped cross-section (FIG. 4g) at the distal end 170.

Method

A method for treating obstructive sleep apnea using the device 100 described herein comprises the steps of: providing an insert member having a proximal end and a distal end, and a lumen there between; providing a shaping member having a proximal end and a distal end; providing a needle optionally having a lumen; mounting the insert member onto the needle; inserting at least a portion of the needle into the patient's tongue; optionally further advancing at least a portion of the insert member into the patient's tongue over the needle; removing the needle from the patient's tongue and leaving at least a portion of the insert member in the patient's tongue; and inserting at least a portion of the shaping member into the lumen of the insert member so that the insert member and shaping member interact to distribute a force on at least a portion of the patient's tongue.

A modified Seldinger technique can be used to place the insert member in the tongue. A needle or trocar is inserted into the midline of the tongue near the frenulum and advanced until it exits the tongue base or is near the tongue base. A guide wire can then be introduced through the needle and then the needle removed. An introducer is then slid over the guide wire and the guide wire removed. The insert member can then be placed in the lumen of the introducer or over the outside of the introducer and the introducer removed, leaving the insert member behind. Alternatively, the insert member is mounted onto a needle shaft and delivered directly into the tongue to the desired depth. The needle is then removed, leaving the insert member behind.

More specifically, a method for treating obstructive sleep apnea using the device 100 described herein comprises the steps of: providing an insert member having a proximal end and a distal end, and a lumen there between, wherein the lumen is collapsible; providing a shaping member having a proximal end and a distal end; providing a needle having a lumen; and, inserting at least a portion of the needle into a patient's tongue; providing a guidewire sized to pass through the lumen of the needle; inserting at least a portion of the guidewire into the lumen of the needle; removing the needle from the patient's tongue leaving at least a portion of the guidewire in the patient's tongue; positioning the lumen of the insert member over the guidewire; and removing the guidewire from the patients tongue after advancing at least a portion of the insert member into the patient's tongue; and inserting at least a portion of the shaping member into the lumen of the insert member so that the insert member and shaping member interact to distribute a force on at least a portion of the patient's tongue.

In one embodiment of the methods described herein, the proximal end of the shaping member is adapted to be positioned near the proximal end of the insert member. In another embodiment of the methods, the insert member has a flange on the distal end or the proximal end or both. In yet another embodiment of the methods, the proximal end of the shaping member resides outside the lumen of the insert member. In another embodiment of the methods, the insert member penetrates completely through the tongue. In another embodiment of the methods, the shaping member is inserted into the insert member just prior to sleep and removed upon waking. And in yet another embodiment of the method, upon removal of the shaping member from the insert member the lumen collapses.

The shaping member may be inserted into the lumen of the insert member by the patient just prior to sleep and removed upon waking. The purpose of the shaping member is to alter the shape or compliance of the tongue, particularly near the base of tongue, so as to reduce the degree of contact with the pharyngeal wall. In this way, the two-part device is uniquely designed to address tongue based obstructive sleep apnea. A variety of shaping members and insert members are available to surgeons to enable them to treat patients on an individual basis, i.e., to match their particular anatomic condition that is causing their apnea or snoring.

One key benefit of this invention is that it can be implanted under local anesthesia, no general anesthesia is required. Other benefits are that it can be implanted by an Otolaryngologist in an out-patient setting, is adjustable and removable, only works when the patient wants it to, and that it can be applied to different tissue sites in the airway (tongue, soft palate, and pharyngeal wall).

In other embodiments, the device 100 can be used to treat other sites in the upper airway. For example, the device can be placed in the soft palate to reduce snoring. It may also be placed in the pharyngeal wall to modify the shape of the pharyngeal wall during sleep.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

We claim:

1. A device for treating a patient with obstructive sleep apnea, the device comprising: an insert member having a proximal end and a distal end and a lumen there between; a shaping member having a proximal end and a distal end; wherein the insert member has a compliance matching that of a tongue of the patient into which it is configured to be implanted and the lumen is collapsible and adapted to receive at least a portion of the shaping member; and wherein the shaping member comprises a bulb assembly in fluid communication with a pressure receiver chamber.

2. The device of claim 1, wherein the shaping member further comprises a pressure relief valve in fluid communication with the pressure receiver chamber.

* * * * *